United States Patent
Frey

(10) Patent No.: US 8,734,515 B2
(45) Date of Patent: May 27, 2014

(54) METHODS AND APPARATUS FOR INSERTION OF INTERVERTEBRAL IMPLANTS AND DEVICES THEREFOR

(76) Inventor: George Frey, Englewood, CO (US)

( * ) Notice: Subject to any disclaimer, the term of this patent is extended or adjusted under 35 U.S.C. 154(b) by 471 days.

(21) Appl. No.: 12/434,328

(22) Filed: May 1, 2009

(65) Prior Publication Data
US 2009/0281551 A1 Nov. 12, 2009

Related U.S. Application Data

(60) Provisional application No. 61/051,036, filed on May 7, 2008.

(51) Int. Cl.
*A61F 2/44* (2006.01)
(52) U.S. Cl.
USPC ............ 623/17.11; 606/99; 606/90
(58) Field of Classification Search
USPC ........... 606/99, 108, 57, 90, 105, 246, 248, 606/249, 282, 914; 623/17.11, 17.15, 17.16
See application file for complete search history.

(56) References Cited

U.S. PATENT DOCUMENTS

| | | | |
|---|---|---|---|
| 3,486,505 A | | 12/1969 | Morrison |
| 5,549,679 A | * | 8/1996 | Kuslich ............. 623/17.12 |
| 5,653,762 A | | 8/1997 | Pisharodi |
| 5,658,336 A | | 8/1997 | Pisharodi |
| 5,876,440 A | | 3/1999 | Feingold |
| 6,309,421 B1 | | 10/2001 | Pisharodi |
| 6,368,325 B1 | | 4/2002 | McKinley et al. |
| 6,436,119 B1 | * | 8/2002 | Erb et al. ............. 606/198 |
| 6,595,998 B2 | | 7/2003 | Johnson et al. |
| 6,887,248 B2 | * | 5/2005 | McKinley et al. ............. 606/99 |
| 6,997,929 B2 | | 2/2006 | Manzi et al. |
| 7,153,305 B2 | | 12/2006 | Johnson et al. |
| 7,311,713 B2 | | 12/2007 | Johnson et al. |
| 2002/0151856 A1 | | 10/2002 | Gollobin |
| 2002/0161375 A1 | | 10/2002 | Ralph et al. |
| 2005/0187559 A1 | | 8/2005 | Raymond et al. |
| 2005/0216088 A1 | | 9/2005 | McKinley et al. |
| 2005/0283161 A1 | | 12/2005 | McCombe et al. |
| 2006/0129238 A1 | | 6/2006 | Paltzer |
| 2007/0142841 A1 | | 6/2007 | Reitzig et al. |

(Continued)

OTHER PUBLICATIONS

Examination Report for Australia Patent Application No. 2009244557, dated Jul. 10, 2013 5 pages.

(Continued)

*Primary Examiner* — Thomas J Sweet
*Assistant Examiner* — Christopher D Prone
(74) *Attorney, Agent, or Firm* — Sheridan Ross P.C.

(57) ABSTRACT

Surgical device and methods for using same for distraction of adjacent vertebrae and insertion of an intervertebral implant material there between are disclosed. In a method, a leading end of the surgical device having major and minor dimensions is inserted between adjacent vertebrae with the minor dimension aligned in the rostral-caudal direction, and then the leading end is rotated to a second orientation to align the major dimension with the rostral-caudal direction. The surgical device includes slots permitting expansion thereof to allow an implant to be disposed from the leading end into the intervertebral space. In another form, the a first member of a surgical device is initially inserted in an orientation, and second member is moved relative to the first member to expand the first member for distracting the vertebrae, the implant then being disposed from the leading end into the intervertebral space.

16 Claims, 3 Drawing Sheets

(56) References Cited

U.S. PATENT DOCUMENTS

| | | | |
|---|---|---|---|
| 2007/0213739 A1 | 9/2007 | Michelson | |
| 2007/0270873 A1 | 11/2007 | Flickinger et al. | |
| 2007/0270875 A1* | 11/2007 | Bacher et al. | 606/90 |
| 2007/0276406 A1 | 11/2007 | Mahoney et al. | |
| 2008/0071279 A1 | 3/2008 | Bandeira et al. | |
| 2008/0114371 A1 | 5/2008 | Kluger | |
| 2008/0132902 A1 | 6/2008 | Bertagnoli et al. | |
| 2008/0161817 A1 | 7/2008 | Parsons et al. | |

OTHER PUBLICATIONS

Notice of Allowance for Canada Patent Application No. 2,722,918, dated Sep. 30, 2013 1 page.

International Search Report and Written Opinion for International (PCT) Application No. PCT/US2009/042570 mailed Jun. 25, 2009, 10 pages.

International Preliminary Report on Patentability for International (PCT) Application No. PCT/US2009/042570 mailed Nov. 18, 2010, 10 pages.

Search Report for European Patent Application No. 09743348.6, dated May 24, 2013 5 pages.

Official Action for European Patent Application No. 09743348.6, dated Jun. 4, 2013 8 pages.

Official Action with English Translation for Japan Patent Application No. 2011-508565, mailed Jun. 28, 2013 6 pages.

* cited by examiner

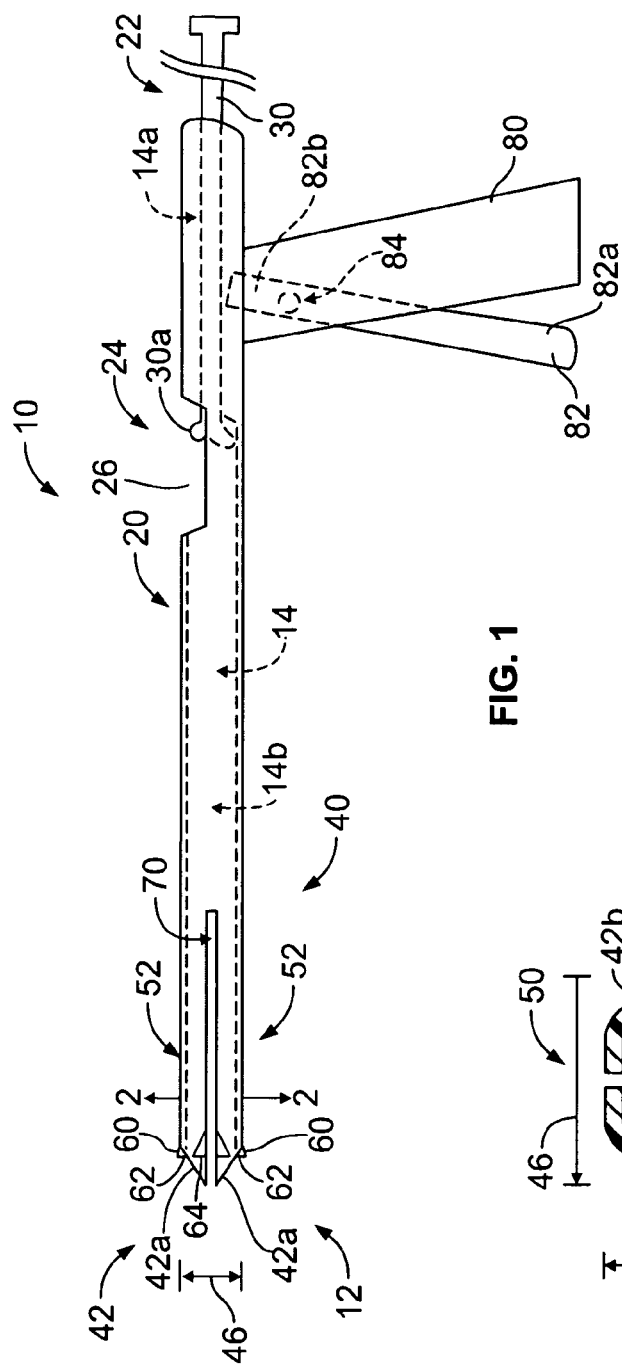
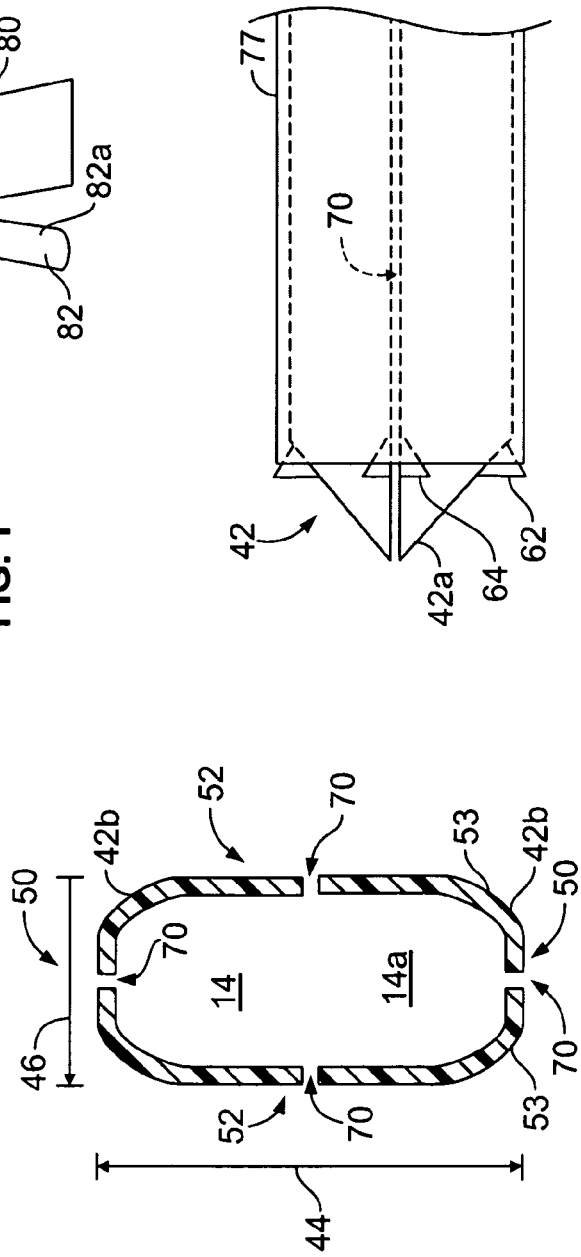

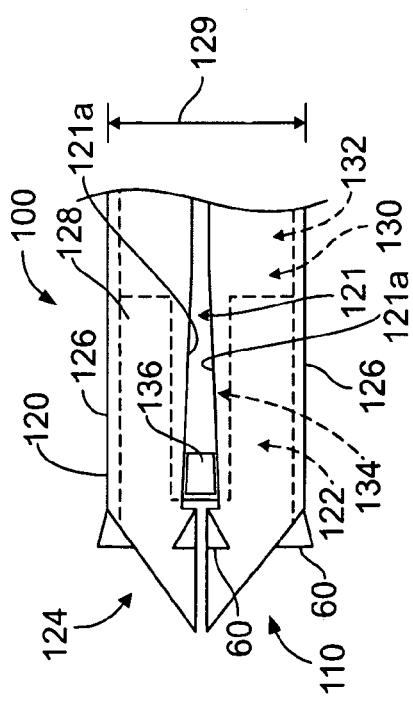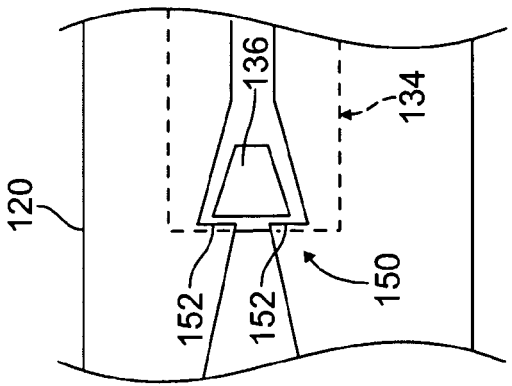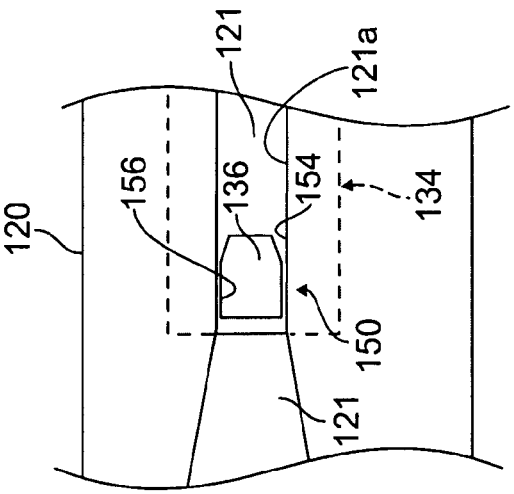

METHODS AND APPARATUS FOR INSERTION OF INTERVERTEBRAL IMPLANTS AND DEVICES THEREFOR

CROSS-REFERENCE TO RELATED APPLICATION

This application claims the benefit of U.S. Provisional Patent Application No. 61/051,036 filed May 7, 2008, the entirety of which is incorporated herein by reference.

FIELD OF THE INVENTION

The invention relates to intervertebral implants, to devices for disposing and locating and assembling an intervertebral implant in an intervertebral space, and to methods related thereto.

BACKGROUND

Currently, one of the most difficult portions of the human to repair and to protect during healing is the spinal column or spine. In simple terms, the spine may be viewed as a series of vertebrae connected by and alternating with intersticial positioned spinal discs. The spinal discs include an outer portion referred to as an annulus formed of relatively tough and only minimally elastic material that is, nonetheless, pliable and may be likened to leather. Each annulus surrounds a nucleus that is constituted from a highly viscous gel-type material. Each annulus is secured with a superior vertebra across a bony endplate of the vertebra, as well as an inferior vertebra across a bony endplate of the inferior vertebra.

Each vertebra has a channel for the spinal nerve separated from endplates and discs. The discs support and enable the biomechanical movement of the torso, such as flexion/extension in anterior, posterior, and lateral directions, and in torsional movement around a general vertical axis of the spine.

Should one or more discs be damaged, a person may experience pain from a number of the modes. In one mode, the annulus may be damaged so that the disc bulges and presses on the spinal nerve. In another mode, the annulus may fail to provide sufficient support so that the portion of the spine in a superior position to the damaged annulus compress downwardly, which also compresses the spinal nerve. Another mode is a damaged vertebra that results in pain or contributes to damage of portions of the spine.

A number of treatments are known for addressing spinal pain and other conditions (such as scoliosis or other unfortunate but naturally occurring conditions). While there are non-surgical treatments available for some pain originating from damage to the spinal column, such are typically limited to minor irregularities. For any significant damage, surgical procedures are often necessary to relieve pain and/or regain a portion of a person's mobility.

One category of such procedures is defined by the use of intervertebral implants. Intervertebral implants specifically are devices that are placed in the interstice that normally is occupied only by the naturally occurring spinal disc. Intervertebral implants may be total disc replacements (TDR) following a discectomy, removal of the entirety of the naturally occurring disc. Other intervertebral implants are intradiscal wherein a portion or entirety of the nucleus is removed (a procedure known as a nucleotomy) and replaced with one or more implants within the natural annulus. Some known implants designs, whether TDR or intradiscal, are designed to mimic or replace the natural biomechanical properties of the natural disc, while others are fusion discs seeking to immobilize the superior and inferior vertebrae, generally permanently. For fusion implants, it is known to design implants and perform procedures that seek to stimulate, promote, or benefit from bone in-growth into the intervertebral space, implants that may or may not include natural or artificial bone graft material.

There are a number of difficulties with current designs and procedures for locating and implanting the variety of intervertebral implants. To begin with, a common manner for implantation requires a distractor device applied to adjacent vertebrae. This is necessary, since the diseased disc space is typically very narrow, and collapsed. This disc space height must be restored if an optimal outcome is to be achieved. Replacing the support provided by the disc requires spanning the distance between the endplates, which have concave surfaces facing the disc. Therefore, the distance between the vertebrae at the outer portion of the nucleus is smaller than the desired height for the implant construct. Applying a distractor to the vertebrae assists in forcing the larger implant between the vertebrae.

One example of a prior art implantation device or insertion distractor is shown in U.S. Pat. No. 3,486,505, to Morrison. This '505 patent requires placing distal portions of opposed arms between adjacent vertebrae. Once there, a plunger or rod is advanced to force an implant between the arms, thereby spreading the arms and distal portions thereof outwardly to distract the vertebrae. This method and design puts a significant amount of stress on the implant itself, as it is the implant that is doing much of the work. Such compression may damage the implant before the implant is ever disposed in the intervertebral space, and high frictional forces are exerted on the sides of the implant that are in contact with the arms. Finally, as the implant is doing the work, manipulation of the implant to a desired purpose is hindered, particularly once the implant has passed beyond the arm distal portions so that it is in full and direct contact with the endplates.

While the design of the '505 needs the implant to slide, generally prevents use with an implant having surface fixation features such as spikes, U.S. Patent Application Publication No. 2008/0161817, to Parsons, et al. attempts to overcome such deficiency. Specifically, the implant has laterally located spikes, the arms of the inserter device engaging on a central portion of the implant with the spikes positioned outboard therefrom. Additionally, the plunger itself appears to provide at least a part of the distraction force for the arms. However, the '817 design maintains the spikes in an exposed position at all times during implantation. Additionally, the implant must be located between the arms at the distal end of the distractor/implantor device prior to placing the device in situ, resulting in the spikes being exposed and seating of the implant being susceptible to being effected during the preliminary steps of interfacing the distractor device with the vertebrae.

U.S. Pat. No. 6,368,325, to McKinley, et al., describes a distractor/implantor device specifically described for use with bone blocks. The device includes an elongated handle with a distal forked end defining a space for receiving a bone block therein. The leading surfaces of the fork tines are beveled and, in particular, are shown as having a bevel that aligns with a bevel surface formed on a leading end of the bone block protruding from between the tines. The bevel surfaces are used to initially wedge first the bone block, then the tines between the vertebrae, a major dimension extending laterally and a minor dimension extending in the spinal superior-inferior (rostral-caudal) direction. The entirety of the device is then rotated around its generally longitudinal axis to distract the vertebrae, the major axis being aligned with the superior-inferior direction. A central rod is then advanced to eject the bone block.

The design of the '325 patent overcomes some of the deficiencies of the above-discussed references, while still presenting other deficiencies. For instance, none of the devices permits selection of an implant device after distraction has occurred. A surgeon may desire to inspect and size the intradiscal or intervertebral space prior to selecting the implant. The above-discussed devices do not permit such inspection without sequential insertion and removal of the distractor/implantor device, or another device (such as a sizer or spacer). Similarly, none of the devices discussed herein allows for sequentially implanting a plurality of implant constructs, or components thereof. The '325 patent also relies on compression directly on the implant during insertion and rotation of the device. The major benefit of the design of the '325 patent is that, once the device is rotated and the vertebrae are distracted, the implant itself can relatively easily be advanced from the device without further distraction.

Another design for a distractor/implantor is illustrated by U.S. Patent Application Publication No. 2007/0270875, to Bacher, et al. Essentially, a central rod pointed tip is utilized as an initial distractor, an outer sleeve has fingers that form a frusto-conical portion extending from the rod pointed tip, and an inner sleeve receives the central rod while itself being received by the outer sleeve. While various uses of the illustrated device may be imagined, one minimally requires the inner and outer sleeves to remain between the vertebrae during distraction and implantation.

Accordingly, there has been a need for an improved distractor/implantor device for locating and implanting artificial spinal discs in intervertebral spaces.

SUMMARY

In accordance with an aspect, a method of inserting implant material into an intervertebral space is disclosed including the steps of positioning a leading end of a surgical device between adjacent vertebrae in first orientation, the leading end having a first dimension aligned with a rostral-caudal direction and a second dimension larger than the first dimension and aligned in a lateral direction, rotating the leading end of the surgical device relative to the adjacent vertebrae to align the larger second dimension with the rostral-caudal direction and distract the adjacent vertebrae, loading the implant material into a cannula, wherein the implant material is not under compression during the step of rotating, and subsequent to the step of rotating, advancing the implant through the cannula and into the intervertebral space from the leading end.

In some forms, the step of positioning includes compressing the leading end in the rostral-caudal direction.

In some forms, the step of loading is prior to the step of positioning.

In some forms, the step of advancing the implant material includes expanding the leading end via force exerted by the implant material, the force received from an advancing rod.

In some forms, the method includes the step of selecting the implant material from one or more of fusion devices and bone graft material.

In some forms, the step of positioning includes determining a position of the surgical device by placing stops formed on the leading end against the adjacent vertebrae.

In some forms, the method further includes the step of preparing, wherein the step of preparing includes one or more of removing natural spinal disc material and determining geometrical features of the intervertebral space.

In an additional aspect, a surgical device for distraction and insertion of intevertebral implant material in an intervertebral space between adjacent vertebrae is disclosed including an elongated barrel, an operative end formed on a distally-located end of the barrel, the operative end for engaging the adjacent vertebrae, wherein the operative end includes a plurality of slots allowing at least the operative end to be expanded, and includes a major dimension and a minor dimension, a cannula leading from a proximally-located portion of the barrel to an opening thereof, the opening at the operative end for disposing of the implant material therefrom, wherein the operative end minor dimension is sized to be received between the adjacent vertebrae in an initial insertion, the major dimension is sized for distracting the adjacent vertebrae to permit the implant material to be disposed thereinto, the vertebrae being distracted by rotation of the operative end after the initial insertion, and the implant material is retained within the cannula without significant compression during rotation of the operative end.

In some forms, the surgical device further includes a loading chamber for loading of the implant material into the cannula and a reciprocable rod disposed at least partially in the cannula for advancing the implant material therethrough and from the opening. The cannula may have a non-uniform size such that the cannula is smaller at the opening. The implant material may be advanced through the opening to expand the operative end. The the implant material may be advanced through the opening to at least partially distract the adjacent vertebrae.

In some forms, the rod may be advanced by actuation of a trigger, rotating knob, or other actuator, operatively connected to the rod.

In another aspect, a surgical device for distraction and insertion of intevertebral implant material in an intervertebral space between adjacent vertebrae is disclosed including an elongated barrel, an operative end formed on a distally-located end of the barrel, the operative end for engaging the adjacent vertebrae, wherein the operative end includes a plurality of slots allowing at least the operative end to be expanded, and includes a rostral-caudal dimension and a lateral dimension, wherein the operative end rostral-caudal dimension is sized to be received between the adjacent vertebrae in an initial insertion, a cannula leading from a proximally-located portion of the barrel to an opening thereof, the opening at the operative end for disposing of the implant material therefrom, and an inner member reciprocable within the barrel and having features located thereon for engaging surfaces of the slots of the barrel, movement of the features against the surfaces expanding the barrel and distracting adjacent vertebrae when the operative end is located thereat.

In some forms, the slots are angled, and the inner member features are wedge-shaped for contacting the angled slots. Retraction of the inner member in a direction away from the operative end may forces the wedges through the slots to expand the barrel in the rostral-caudal dimension.

In some forms, surgical device may include stops for maintaining the features in the desired position along the slots.

In some forms, the surgical device further includes a loading chamber for loading of the implant material into the cannula, and including a reciprocable rod disposed at least partially in the cannula for advancing the implant material therethrough and from the opening.

In some forms, the implant material may be advanced through the opening to at least partially distract the adjacent vertebrae.

In some forms, the rod may be advanced by actuation of a trigger, rotating knob, or other actuator, operatively connected to the rod.

BRIEF DESCRIPTION OF THE DRAWINGS

In the Figures, FIG. 1 is a side elevational view of a first form of a surgical device for distracting adjacent vertebrae and inserting an intervertebral disc implant into an intervertebral space between the adjacent vertebrae, the device including an advancable rod for directing the implant received in a loading chamber through a cannula of the device, the rod being shown as broken to indicate length;

FIG. 2 is a cross-sectional view taken through the line 2-2 of FIG. 1 showing the profile of an operative end portion of a barrel of the surgical device, the device having been rotated 90 degrees from the first orientation of FIG. 1 to the second orientation of FIG. 2;

FIG. 5 is an enlarged fragmentary view of the operative end of FIG. 1 showing a sheath or skirt, comprised of a stretchable, or elastomeric material, disposed thereon for protecting surrounding tissues;

FIG. 6 is an enlarged fragmentary view of a barrel of a second form of a surgical device, the barrel having slots cooperating with a wedges formed on a second member to expand the slots and the barrel when the second member is retracted;

FIG. 7 is an enlarged fragmentary view of a portion of a form of the barrel and second member of FIG. 6 the showing a stop for receiving the wedge, the stop formed on the slot; and FIG. 8 is an enlarged fragmentary view of a portion of a form of the barrel and second member of FIG. 6 showing a stop, the stop formed on and between the slot and the wedge.

DETAILED DESCRIPTION

Figure 3:
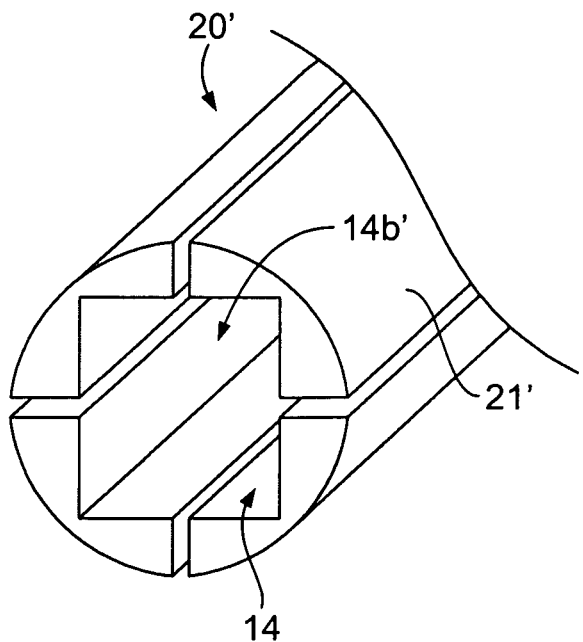
FIGS. 3 and 4 are enlarged fragmentary views of an alternate barrel for the device showing an inner cannula, FIG. 3 showing the cannula having larger dimensions than the cannula shown in FIG. 4, the large dimension portion of FIG. 3 being positioned within the device more rearwardly than the smaller dimension portion of FIG. 4 so that advancement of a rigid implant therethrough expands the barrel via the illustrated slots.

Referring initially to FIG. 1, a surgical device 10 is illustrated for distraction of adjacent vertebrae and implantation of artificial intervertebral implants. The surgical device 10 may be described as both a distractor and as an implantor; for convenience herein, the surgical device 10 is referred to as an IDD 10. In use, a leading or operative end 12 of the IDD 10 is initially inserted between adjacent vertebrae in a first orientation, the IDD 10 then being rotated to a second orientation to fully distract the vertebrae for receiving an implant therebetween. One or more implants are loaded into a central cannula 14 of the IDD 10 and then forced advanced through the cannula 14, out from the operative end 12, and into the intervertebral space.

In greater detail, a form of the IDD 10 includes an elongated insertion and distraction portion referred to herein as a barrel 20 having the operative end 12 distally located from a stock end 22. The barrel 20 includes a loading chamber 24 which includes an opening 26 extending from the cannula 14 through the barrel 20 to the environment so that one or more implants may be inserted through the opening 26 and into the cannula 14.

The cannula 14 extends the entire length of the barrel 20. At the stock end 22, a rod 30 is disposed. The rod 30 may, in one use, be viewed as a push rod; however, a distal end 30a of the rod 30 may be connected with a dummy or trial device, such as a sizer, so that the trial device is inserted into the intervertebral space to determine a proper size for a subsequently-inserted implant, in which case the rod 30 would also pull in order to remove the trial device. The rod 30 may also consist of a plurality of rods (not shown), some or all of which may penetrate the implant or implants, partially or completely. These rods may move independently of one another, and to varying degrees, and may contact one or all components of a multi-component implant or a plurality of implants. Thus, the rod 30 (or rods) may also serve as a guide mechanism for the implant(s) thru the cannula 14, and beyond the barrel 20, and into the intervetebral space, to a predetermined location, for predicable deployment, as well as enable assembly of the of the implant(s) and components into a final construct in the intervertebral space. The loading chamber 24 allows access to the rod distal end 30a when the rod is in an at least partially retracted or withdrawn position. As an example, the rod distal end 30a may be threaded so as to be received within internal threads of an implant.

In another form, the rod 30 may be removed to allow a second rod or plunger (not shown) to be used for, as an example, a sizer or a targeting device. The targeting device may have a geometry matching or closely approximating that of the implants to be used. Use of the targeting device allows the user to manually and tactilely determine the shape (including contours) of the intervertebral size, as well as assess and select alignment of the IDD 10 with the vertebrae and intervertebral space. The second rod may provide a depth gauge, such as graduated or other depth markings, enabling a surgeon to determine the depth at which the implant should be inserted. In the subsequent implant insertion, the surgeon can operate the rod 30 to the same depth, or at least one determined based upon the use of the targeting device. Towards that end, the rod 30 may have graduated markings identical, similar, or corresponding to those of the second rod.

Accordingly, the rod 30 reciprocates to and between advanced and retracted/withdrawn positions within the cannula 14. The rod 30 may be withdrawn to be clear of the loading chamber 24, thus permitting an implant to be deposited into the loading chamber 24. The rod 30 may then be advanced or extended to a position so that the implant is forced beyond the barrel operative end 12 and, thus, inserted into the intervertebral space.

A distal section 40 of the barrel 20, including the operative end 12, is used for distraction of the adjacent vertebrae. A terminal portion 42 of the operative end 12 of the barrel distal section 40 has a reduced dimension to allow a portion thereof to be received between the adjacent vertebrae. More specifically, the operative end 12 includes a major dimension 44 extending in a first direction and a minor dimension 46 extending in a second direction. During initial insertion of the IDD 10 and, specifically, of the terminal portion 42 between the vertebrae, the major dimension 44 is aligned laterally and generally parallel to the general plane of the natural disc and intervertebral space (which is generally horizontal in an erect human, transverse to the longitudinal extent of the spine).

After initial insertion of the terminal portion 42, the user then proceeds to force vertebral distraction. The user may apply an axial force along the longitudinal direction, thus utilizing a wedge or chamfer 42a formed on the terminal portion 42 to provide an initial distraction amount.

Regardless, the user rotates the terminal portion 42 to cause distraction of the adjacent vertebrae. Generally speaking, the entire IDD 10 is rotated so that the major dimension 44 of the operative end 12 is shifted from the first orientation generally aligned with the small intervertebral space to a second orientation to be aligned with the superior-inferior longitudinal spinal axis (rostral-caudal). This movement necessarily forces the adjacent vertebrae apart, the outer surface 42*b* (such as radiused corners, FIG. 2) of the terminal portion 42 acting as a cam surface. In the preferred form, minor sides 50 of the terminal portion 42 are shaped so that the compression exerted on the minor sides 50 by the adjacent vertebrae maintains the terminal portion 42 in position in the second orientation and, more broadly, so that the entire IDD 10 is maintained with the major dimension 44 aligned with the longitudinal direction of the spine.

It is also preferred that the terminal portion 42 includes stops 60 formed on the terminal portion 42. In a first form, the stops 60 are formed as shoulders 62 on major sides 52 to limit the amount of insertion of the IDD 10 between the vertebrae. The stops 60 provide a predetermined position relative to at least sides of the vertebrae and, more preferably, a predetermined position relative to the invertebral space. More specifically, with a knowledge of the intertebral dimensions and contours, and a knowledge of the size and shape of the vertebrae, the IDD 10 can be placed at a specific and known location relative to those features via use of the stops 60. As such, a user is able to insert an implant in a specific spot within the intervertebral space. In a further form, stops 60 may also be formed as shoulders 64 on the minor sides 50. The stops 60 may be formed on a selectively positionable member (not shown) so that a user may adjust the position of the stops relative to the ultimate tip of the terminal portion, or position the angle of the stops 60 relative to the longitudinal axis of the cannula 14 allowing the stops 60 to accommodate the vertebral aspect shape.

The distal section 40 of the barrel 20 includes longitudinal slots 70. The slots 70 allow the distal section 40 to be compressed during initial insertion.

After rotation of the terminal portion 42, the IDD 10 may be operated to advance an implant through the cannula 14 and into the intervertebral space. It should be noted that, should a user desire, the cannula 14 may be used to perform all modes of disc space preparation, such as a discectomy or nucleotomy or for a trial or sizing device, for instance, and as a minimally invasive surgical technique.

The cannula 14 may have a uniform shape or non-uniform shape in both the longitudinal direction and in cross-section. For instance, the rod 30 may be closely fit through a proximal section 14*a* of the cannula 14, thus serving as a guide to control the reciprocation of the rod 30. A cannula distal section 14*b* may have a different size or cross-sectional shape from that of the proximal section 14*a* so that the rod 30 passes easily therethrough.

In the preferred form, the distal section 14*b* has a cross-sectional shape corresponding to the shape of an implant. This cross-sectional surface shape may include additional features or projections, such as ribs or rails, that further guide or orient the implant into a predetermined position. As can be seen in FIG. 2, one form of the cannula 14 has a rectangular cross-sectional shape for use with an implant of similar or identical cross-sectional shape.

Notably, the cross-sectional shape of the distal section 14*b* corresponds to, but need not be identical to, the cross-sectional shape of an implant. In use, once the terminal portion 42 has been rotated to distract the vertebrae, the cannula distal section 14*b* may taper inwardly, prior to the implant being advanced through the cannula distal section 14*b* by the rod 30. In this position, the terminal portion 42 generally remains in the somewhat compressed state due to the insertion and distraction process, both in the direction of the minor dimension 44 as friction and pressure between the terminal portion 42 and the vertebral endplates does not generally permit normal, elastic return to a natural position, and in the direction of the major dimension as the vertebrae exert a compressive force on the minor sides 50.

The distal section 14*b* is expanded by the advancing implant. As the implant is forced through the distal section 14*b* by the rod 30, the major sides 52 are forced laterally outwardly. In some forms, the minor sides 50 are also forced outwardly (superior-inferior direction, rostral-caudal direction) to provide additional distraction. Again, expansion and contraction of the distal section 14*b* is permitted by the slots 70.

As described, the distal section 14*b* acts somewhat as a guide rail. Discussed above, the stops 60 provide a user with a known or ascertainable starting position, relative to the vertebrae. The close-fit and co-operation of the distal section 14*b* with the implant shape allow a user to have a definite knowledge of where and in what orientation the implant exits the cannula 14. Again, the use of the above-described targeting device/sizer and/or graduated markings on the rod 30 also help the user locate the implant at a known position.

After the initial implant or implant component has exited from the distal section 14*b* and into intervertebral space, a multitude of subsequent components may be delivered into the intervetebral space in a similar fashion, trailing the initial component, and forcibly driven together into a final assembly by the rod 30 or rods. Throughout this sequential process, the distal section 14*b* is ready for further implants or implant material. The distal section 14*b* likely compresses somewhat in the rostral-caudal direction (shortening the major dimension 44 by compressing the slots 70 thereof). The distal section 14*b* may or may not compress in the lateral direction (e.g., for shortening the minor dimension 46) due to residual force thereon from the endplates. The rod 30 or rods may be retracted or withdrawn so that its leading end is clear of the loading chamber 24 and received in the cannula proximal section 14*a*. A subsequent implant or implant material may then be loaded into the loading chamber 24 for advancement into the intervertebral space via a second advancement of the rod 30. Such allows additional implantation without requiring removal or re-insertion of the IDD 10, as described for prior art in the background. Furthermore, the placement of multiple implant components in the chamber, placed one behind the other, or placed side-by-side, allows the rod 30 or rods to deliver implants to the intervetebral space in a simultaneous and or sequential fashion. For instance, implants that are constructed of simultaneously or sequentially inserted components are advantageously accommodated by the IDD 10, as well as fusion procedures in which graft material may be subsequently packed into the intervertebral space and/or into cavities formed in and around the implant itself.

The IDD 10 is designed to protect, or avoid, adjacent tissues including neural tissues. Prior to and during initial insertion of the IDD 10, a sheath or skirt 77 is positioned around the terminal portion 42. The skirt 77 prevents or limits the ability for tissues to be caught by the slots 70 or the stops 60. In various exemplary forms, the skirt 77 may then be retracted to expose the slots 70 and stops 60, and/or the skirt 77 may be positioned to extend rearwardly from the stops 60 simply expand to accommodate the expansion of the slots 70 when an implant is advanced through the distal section 14*b* of the cannula 14.

As illustrated, the IDD 10 is operated in a pistol-trigger fashion, though a rotating knob (not shown) or other actuator type may be employed. As can be seen in FIG. 1, the barrel 20 is supported by and secured with a grip 80. The grip 80 allows the user to manipulate the IDD 10 generally with a single hand. A trigger 82 is hinged with the grip 80 and is spring-biased so that an actuator end 82a angles downwardly and away from the grip 80. When the trigger 82 is actuated by a user, the actuator end 82a is pulled (such as by fingers of the single hand) towards the grip 80, an upper, rod end 82b of the trigger 82 moving forwardly toward the operative end 12 of the IDD 10. The rod end 82b contacts or mates with the rod 30 to incrementally advance the rod 30 and an implant in the cannula distal section 14b or loading chamber 24.

Initial advancement of the rod 30 may be manually, such as by simply forcing the rod 30 forward by applying force to the end thereof protruding from the barrel 20. Once force is required, the trigger 82 may be employed. The engagement between the trigger rod end 82b and the rod 30 is such to permit slipping therebetween when the rod 30 is being advanced forward relative to the trigger 82. In one form, the trigger rod end 82b and the rod 30 may frictionally engage, while in another form the rod 30 may have a series of notches (not shown) that act in a ratchet manner with the trigger rod end 82b, though other mechanisms may be employed.

In a preferred form, the IDD 10 is easily cleaned and sterilized. To facilitate removal of particulate matter, the IDD 10 may be disassembled by removing a pivot pin 84 for the trigger 82 and removing the barrel 20 from the grip 80, the rod 30 also be removable through the cannula proximal section 14a and the skirt 77 being removable from either end of the barrel 20.

The implants may be any type of partial or total disc replacement implant, and may be any type of implant such as natural or artificial bone graft material, fusion boxes or cages, expandable devices, sequentially-constructed devices, hydrogel- or hydrophilic-based devices, or others made of metallic, polymeric, elastomeric, ceramic, materials, or combinations of these types.

In one form, the IDD 10 may be secured with a spinal fixation system such as a pedicle screw installed on a vertebrae prior to use of the IDD 10. This promotes maintaining the IDD 10 in the selected and desired position determined by the user during use of the trial or targeting devices, discussed above, for instance.

Figure 4:
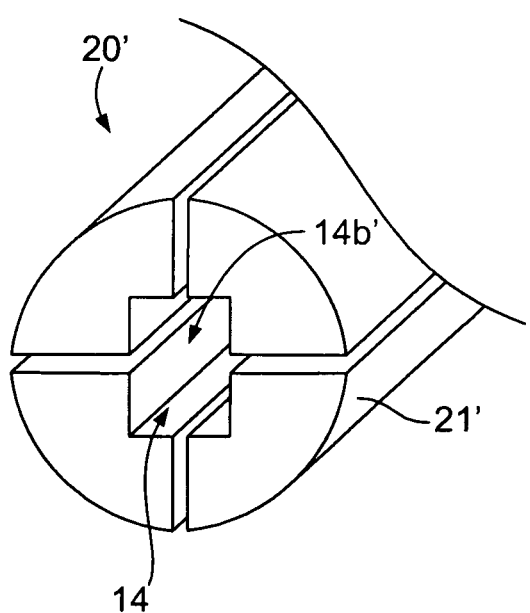

It should be noted that the operative end 12 and terminal portion 42 may have a variety of exterior or surface configurations. The terminal portion 42 has been illustrated and impliedly discussed as being generally rectangular, as shown for FIG. 1. Beyond this, the preferred form has, at minimum, radiused corners 53 to facilitate rotation of the terminal portion 42 between and against the vertebrae. In various forms, the corners 53 need not be identical, such as by providing a single direction of rotation for the terminal portion 42. Moreover, the major and minor dimensions 44, 46, and their respective sides, may also be viewed as corresponding to a racetrack-shape having curved or circular minor sides connected by straight sides, or may be viewed as an oval or elliptical having major and minor axes, as mere examples. As illustrated in FIGS. 3 and 4, an alternate form of a barrel 20' may have a circular or cylindrical outer surface 21', with a rectangular cross-section for cannula distal section 14b' that varies from a larger size (FIG. 3) proximal the loading chamber 24 to a smaller size (FIG. 4) closer to or at the terminal portion 42.

A second form of an inserter/distractor device or IDD 100 is illustrated in FIG. 6. In simple terms, the IDD 100 has a small dimensioned profile or leading portion 110 for initial insertion between adjacent vertebrae. Unlike the above-discussed IDD 10, however, the IDD 100 is not rotated, instead operating to expand and distract the vertebrae by relative shifting of two components.

In the illustrated form, the IDD 100 includes an outer member 120 somewhat in the form of a sleeve having a cannula 122. The outer member 120 may include stops 60 for providing a predetermined or known position relative to the vertebrae. A leading end 124 is positioned between the vertebrae, up to the stops 60. After the initial insertion of the leading end, an inner member 130 is moved relative to the outer member 120 to expand the outer member 120. More specifically, the outer member 120 is illustrated as having a somewhat quadrilateral shape, similar to that of IDD 10, with rostral-caudal sides 126 corresponding to a lateral dimension (into the plane of FIG. 6) and having lateral sides 128 corresponding to a rostral-caudal dimension 129. When expanded, the distance between the rostral-caudal sides 126 (across the cannula 122) are increased, increasing the rostral-caudal dimension 129. At least each of the lateral sides 128 includes a longitudinally extending slot 121 that permits such expansion. In other forms, a plurality of slots (not shown) may be provided on the outer member 120, such as slots (not shown) on the rostral-caudal sides 126 and additional slots (not shown) on the lateral sides, each of these other slots allowing for additional expansion due to an implant passing therethrough, as is described above for the IDD 10, and a skirt 77 (FIG. 5) may also be provided.

In the illustrated form, the inner member 130 is a partial sleeve, having a sleeve-like body portion 132 closely received within the outer sleeve cannula 122 and having forwardly or distally extending arms 134. The arms 134 each have a small wedge 136 facing outward and engaged in respective minor side slots 121, which themselves may have angled surfaces 121a as shown in FIG. 6. As the inner member 130 is retracted, the wedges 136 are forced rearwardly through the slots 121, thus expanding the slots 121 and the minor sides 128 so that the major sides 126 are moved apart to distract the vertebrae.

There is a number of variations on the IDD 100. For instance, the shapes of the wedge 136 and slot 121 could be reversed so that advancing the inner member 130 (as opposed retracting, as discussed) forces the slots 121 to widen. The inner member 130 may be simply the pair of arms 134, without the body portion 132, or the body portion may be some other type of bridge allowing the arms 134 to be manipulated jointly. In another form, the inner member 130 may be entirely sleeve-like through the portion of the IDD 100 that the implant would pass, but for the wedges 136 protruding therefrom. In another form, the rod 30 may be connected to the inner member 130 so that, either prior to or in combination with the implant reaching the distal-most portion of the IDD 100, movement of the rod 30 causes the wedges 136 to shift and widen the slots 121 to expand the IDD 100.

These forms of the IDD 100 have distinct benefits over the prior art. For instance, the construction of the IDD 100 minimizes the amount of distraction that is necessary for an implant to pass therethrough. As the wedges 136 are to the lateral sides 128 (in the lateral direction), the amount of rostral-caudal distraction need not accommodate the wedges 136 nor, in a number of described forms, the inner member 130. This is in contrast to the design of the '875 application discussed in the background where a significant amount of distraction is required simply to allow the distractor components to remain between the vertebrae as the implant passes therethrough. Movement of the wedges 136 can also be calibrated so that a particular amount of retraction of the inner member 130 corresponds to a known amount of distraction.

In some forms, the slots 121 and wedges 136 may cooperate to form stops 150 for maintaining the wedges 136 in a desired position. FIG. 7 illustrates a stop 150 in the form of small barbs 152 that the wedge 136 passes beyond when being retracted. The wedge 136 is thus unlikely to inadvertently slip or return over the barbs 152 during use of the IDD 100, that is, without a user intentionally forcing the wedge 136 over the barbs 152.

FIG. 8 illustrates a stop 150 in another form, specifically flats 154 formed on the surfaces of the slot 121 and flats 156 formed on the wedges 136. When the wedges 136 reach the slot flats 154, the pressure on the wedges 136 that would tend to expel the wedges 136 therefrom is reduced or even eliminated, with simply a compressive force on the wedges 136. While the wedge flats 156 are not required, they assist with movement of the wedges 136 against the slot flats 154, as the wedges 136 may otherwise bite into or grind against the slots 121. Although not shown, edges of the wedges 136 may be rounded so that the inner member 130 and wedges 136 may be rotated relative to the slots 121 and outer member 120 in order to release the wedges 136 from the slots 121 and, more particularly, quickly release the stops 150.

It should also be noted that the slots 121 may have a varying contour for more controlled distraction. That is, as the distraction at the distal-most end of the IDD 100 is based on an angular opening of the slots 121, the geometry of the wedges 136 and slots 121 may be designed so that equal amounts of movement of the wedges 136 along the slots results in equal amounts of gross distraction for the IDD 100.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

What is claimed is:

1. A surgical device for distraction and insertion of intevertebral implant material in an intervertebral space between adjacent vertebrae, the device comprising:
an elongated barrel;
an operative end formed on a distally-located end of the barrel having a non-uniform cross section comprised of a first dimension and a second dimension different from the first dimension, the operative end for engaging the adjacent vertebrae, wherein the operative end includes a plurality of slots allowing at least the operative end to be expanded, wherein the plurality of slots include at least one slot in both a major dimension and a minor dimension corresponding to the first dimension and the second dimension, respectively;
a cannula leading from a proximally-located portion of the barrel to an opening thereof, the opening at the operative end for disposing of the implant material therefrom;
wherein the operative end minor dimension is sized to be received between the adjacent vertebrae in an initial insertion position, the major dimension is sized for distracting the adjacent vertebrae to permit the implant material to be disposed thereinto, the vertebrae being distracted by rotation of the operative end after the initial insertion, and the implant material is retained within the cannula during rotation of the operative end; and
wherein, when the implant material is advanced through the operative end, the major dimension is permitted to increase by increasing a dimension of the plurality of slots as a result of the expanding force exerted by the implant material on the operative end.

2. The surgical device of claim 1 further including a loading chamber for loading of the implant material into the cannula and at least one reciprocable rod disposed at least partially in the cannula for advancing the implant material therethrough and from the opening.

3. The surgical device of claim 2 wherein the implant material is a plurality of separate implant components, the loading chamber allows for said plurality of implant components to be simultaneous received therein, each rod operates to advance the implant material from the opening to assemble the implant components within the intervetebral space, and the implant components are advanced separately and in sequence.

4. The surgical device of claim 2 wherein the implant material is a plurality of separate implant components, the loading chamber allows for said plurality of implant components to be simultaneous received therein, each rod operates to advance the implant material from the opening to assemble the implant components within the intervetebral space, and the implant components are advanced simultaneously.

5. The surgical device of claim 1 wherein the cannula has a non-uniform size such that the cannula is smaller at the opening.

6. The surgical device of claim 5 wherein the implant material is advanced through the opening to expand the operative end.

7. The surgical device of claim 5 wherein the implant material is advanced through the opening to at least partially distract the adjacent vertebrae.

8. The surgical device of claim 1 wherein the rod is advanced by actuation of a trigger operatively connected to the rod.

9. The surgical device of claim 1 wherein the elongated barrel is removable and selectable based on the minor and major dimensions of the operative end of the elongated barrel.

10. The surgical device of claim 1 wherein the major dimension of the operative end of the elongated barrel is permitted to increase by being comprised of a material having a low modulus of flexibility.

11. A surgical device comprising:
an elongated barrel;
a rod oriented within the elongated barrel and selectively movable about the longitudinal axis of the barrel;
a chamber for receiving an implant material;
an operative end formed on a distally-located end of the barrel and having a major and minor dimension, wherein the operative end includes a plurality of expansion slots allowing at least the operative end to be expanded when an implant material passes therethrough;
a cannula leading from a proximally-located portion of the barrel to an opening thereof, the opening at the operative end for disposing of the implant material therefrom;
wherein the operative end minor dimension is sized to be received in an initial insertion position, the major dimension is sized for distracting from the initial insertion position by rotation of the operative end after the initial insertion, and wherein the operative end is further distracted by the implant material being pushed through cannula and the elongated barrel and advancing through the operative end.

12. The surgical device according to claim 11 wherein the operative end is comprised of first and second generally planar surfaces arranged in a generally parallel configuration to each other and third and fourth generally planar surfaces arranged in a generally parallel configuration to each other.

13. The surgical device according to claim 12 wherein the first, second, third and fourth generally planar surfaces extend longitudinally about the longitudinal axis of the elongated barrel at a distance of approximately 5-15 mm.

14. The surgical device according to claim 12 wherein the first, second, third and fourth generally planar surfaces each comprise at least one slot which may be expanded by exerting force on the first, second, third and fourth generally planar surfaces.

15. The surgical device according to claim 12 further comprising at least one expansion slot extending longitudinally from the distal end of the elongated barrel by approximately 5-10 mm for each of the first, second, third and fourth generally planar surfaces.

16. The surgical device according to claim 12 wherein first generally planar surface is connected to the third and fourth generally planar surfaces and further comprises radiused corners between the first generally planar surface and the third and fourth generally planar surfaces, and wherein the second generally planar surface is connected to the third and fourth generally planar surfaces and further comprises radiused corners between the second generally planar surface and the third and fourth generally planar surfaces.

\* \* \* \* \*